Figure 1:
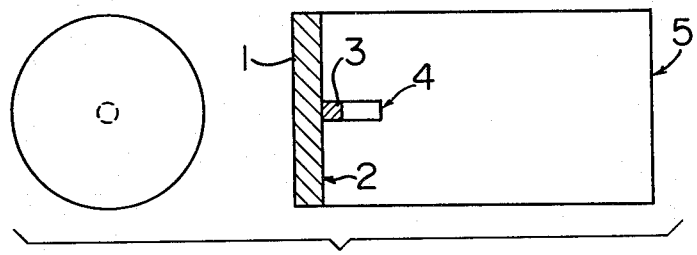

United States Patent [19]

Kimura et al.

[11] Patent Number: 4,466,270

[45] Date of Patent: Aug. 21, 1984

[54] REFERENCE BLOCK USED IN ULTRASONIC EXAMINATION

[75] Inventors: Katsuyoshi Kimura, Tokyo; Shojiro Matsumoto, Kashiwa, both of Japan

[73] Assignee: National Research Institute for Metals, Tokyo, Japan

[21] Appl. No.: 300,286

[22] Filed: Sep. 8, 1981

[30] Foreign Application Priority Data

Sep. 12, 1980 [JP] Japan .................................. 55-126006

[51] Int. Cl.³ ............................................ G01N 29/04
[52] U.S. Cl. ...................................... 73/1 R; 73/1 DR
[58] Field of Search ...................... 73/1 R, 1 DR, 627

[56] References Cited

U.S. PATENT DOCUMENTS

| | | | |
|---|---|---|---|
| 2,912,854 | 11/1959 | Shubring | 73/627 |
| 3,677,061 | 7/1972 | Visser | 73/1 R |
| 4,173,139 | 11/1979 | Conn | 73/1 DR |
| 4,203,315 | 5/1980 | Vieu et al. | 73/1 R |

OTHER PUBLICATIONS

Calibration Block Type G Used in Ultrasonic Normal Beam Testing, Published by Japanese Standards Association, JIS Z 2345, 1978.
Journal of N.D.I., vol. 19, No. 7, p. 385, (in Japanese).
Krautkramer et al., Ultrasonic Testing of Materials, translation of the Third Revised German Edition, Springer-Verlag, Berlin, New York, 1977, pp. 23–25, 197–199, 620.
Ultrasonic Material Testing, Edited by Japan Society for the Promotion of Science, 1974, pp. 617, 618, (in Japanese).

*Primary Examiner*—S. Clement Swisher
*Attorney, Agent, or Firm*—Wenderoth, Lind & Ponack

[57] ABSTRACT

A reference block for ultrasonic examination, said block having an ultrasonic absorber secured to its back surface; and a method for ultrasonic examination using these blocks.

12 Claims, 15 Drawing Figures

REFERENCE BLOCK USED IN ULTRASONIC EXAMINATION

This invention relates to a standard reference block and a reference block for ultrasonic examination. More specifically, this invention pertains to a standard reference block and a reference block for ultrasonic examination with excellent reliability in working sensitivity which shows little or no ghost indication at increased pulse repetition frequencies, and to a method for ultrasonic examination using these blocks.

In the present application, both the standard reference block and the reference block for ultrasonic examination are inclusively referred to as a "reference block for ultrasonic examination". Ultrasonic examination blocks now in use include, for example, G-type sensitivity standard blocks of steel (STB-G) for ultrasonic examination stipulated in JIS Z-2345, sensitivity standard blocks of aluminum alloys stipulated in ASTM E-127, reference blocks stipulated in ASTM E-428, and standard blocks for angle beam testing (C-type standard blocks of U.S. Air Force). In these blocks, however, no measures are taken against ghost indication.

In those days when ultrasonic flaw detection equipment of the classic type was used, pulse repetition frequencies were as low as about 50 or 60 Hz, and no ghost signal appeared on an oscilloscope screen picture. Hence, no trouble occurred. Since about 1965, ultrasonic flaw detectors producing increased pulse repetition frequencies have come into use in order to get a better view of oscilloscope screen pictures and increase scanning speeds in automatic examination. If conventional blocks for ultrasonic examination are used with these modern ultrasonic flaw detectors, ghost indication becomes confusing, and difficulty arises in adjusting working sensitivity.

It is an object of this invention to provide a reference block for ultrasonic examination which reduces ghost indication.

The object of the invention is achieved by a reference block for ultrasonic examination wherein an ultrasonic absorber is secured to its back surface (that surface of the reference block which is opposite the surface to be examined; indicated at 2 in FIGS. 1 to 4).

The ultrasonic absorber used in this invention may be made of any material which can absorb ultrasonic waves. Preferred ultrasonic absorber materials have an attenuation coefficient of at least 0.1 dB/mm, preferably at least 0.5 dB/mm, especially preferably at least 2 dB/mm, at a test frequency of 2.25 MHz and an acoustic impedance of at least $1.5 \times 10^6$ kg/m²s, preferably at least $3 \times 10^6$ kg/m²s, especially preferably at least $5 \times 10^6$ kg/m²s. If the attenuation coefficient is less than 0.1 dB/mm or the acoustic impedance is less than $1.5 \times 10^6$ kg/m²s, the ghost indication becomes confusing and undesirably reduces the reliability of the working sensitivity.

Examples of the ultrasonic absorber used in this invention include metals and synthetic resins.

Examples of such metals are lead and alloys containing at least 30% of lead (e.g., solder). Mixtures of metals with materials capable of scattering ultrasonic waves can also be used conveniently as the ultrasonic absorber. A mixture of lead or an alloy containing at least 30% by weight of lead with tungsten particles is an example. The tungsten particles preferably have an average particle diameter of 1 to 5 mm, but the shape of the particles need not always be spherical. The tungsten particles may be of any shape if they can effectively scatter ultrasonic waves.

Examples of such synthetic resins are phenolic resins. Mixtures of synthetic resins with non-metallic powders can also be conveniently used as the ultrasonic absorber. Examples of the synthetic resins in the mixtures are epoxy resins, methacrylate resins, unsaturated polyester resin and polyurethane resins, and examples of the non-metallic powders are wood flour, asbestos, alumina, iron oxide, lead oxide, vinyl chloride resins, nylon, and hard rubbers.

Mixtures of synthetic resins with metallic powders and optionally, hard rubber powders can also be conveniently used. Examples of the synthetic resins in the mixtures are phenolic resins, epoxy resins, methacrylate resins, unsaturated polyesters and polyurethane resins, and examples of the metallic powders are tungsten, iron, iron alloys, copper, copper alloys, nickel, nickel alloys, and lead.

These ultrasonic absorbing materials may be used singly or in combination in suitable forms.

Especially preferred ultrasonic absorbers are a phenolic resin, a mixture of an epoxy resin and an iron powder, a mixture of an epoxy resin and tungsten powder, a lead alloy, and a mixture of a lead alloy and tungsten particles. The mixture of an epoxy resin and an iron powder, the mixture of an epoxy resin and tungsten powder, and the mixture of a lead alloy and tungsten particles are most preferred.

The body of the reference block used in this invention is made of metals, preferably such as steels, aluminium alloys, titanium alloys, etc.

Figure 7E:
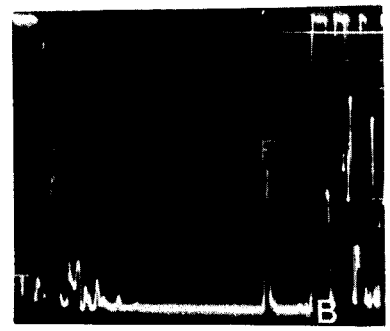
Figure 7F:
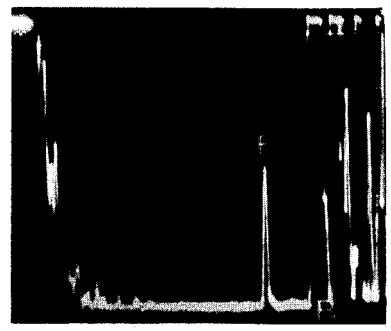
Figure 7G:
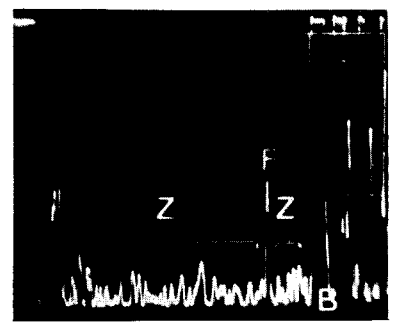

Embodiments of the reference block of the invention for ultrasonic examination are described with reference to the accompanying drawings in which:

FIGS. 1 to 4 are side elevations in vertical section of various embodiments of the reference block of the invention; and FIGS. 5 to 7 are oscilloscope screen pictures appearing in ultrasonic flaw detecting equipment.

Figure 2:
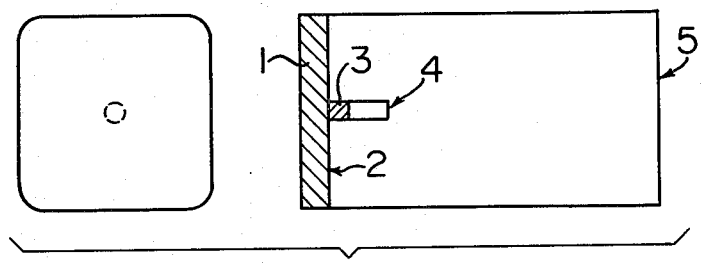
Figure 3:
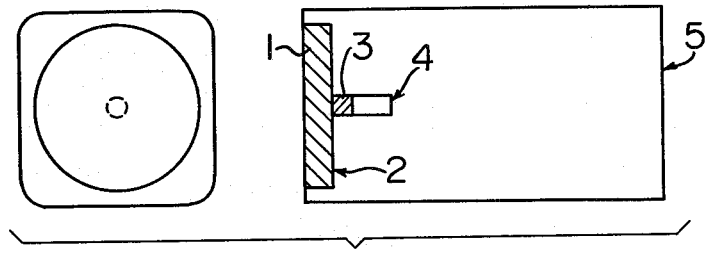
Figure 4:
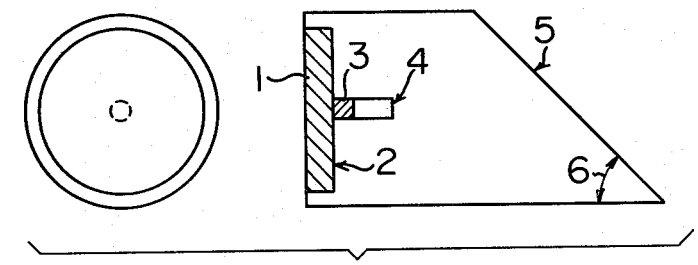
Figures 1, 5A:
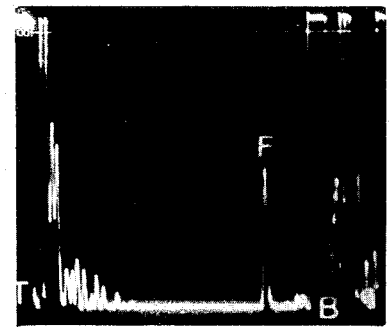
Figures 1, 5B:
Figures 2, 5A:
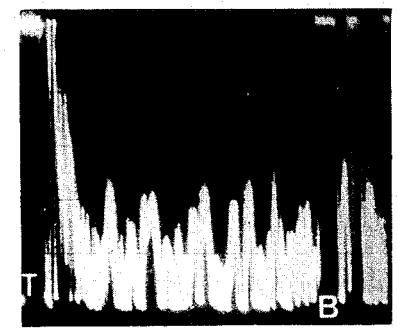
Figures 2, 5B:
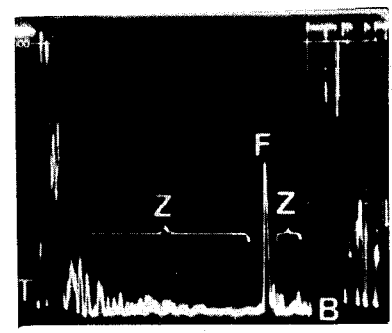
Figures 1, 6C:
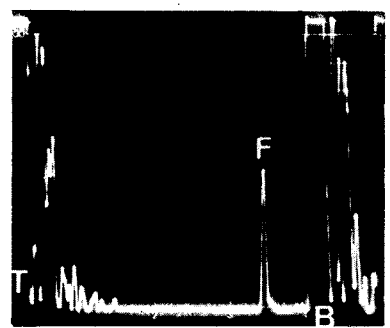
Figures 1, 6D:
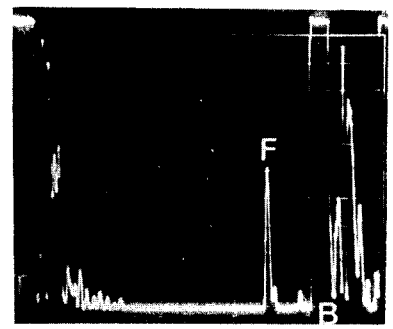
Figures 2, 6C:
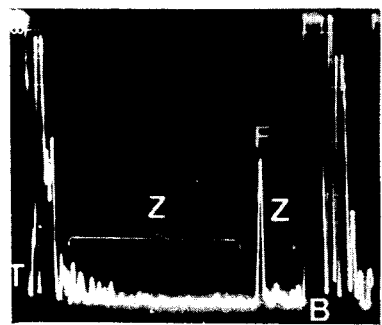
Figures 2, 6D:
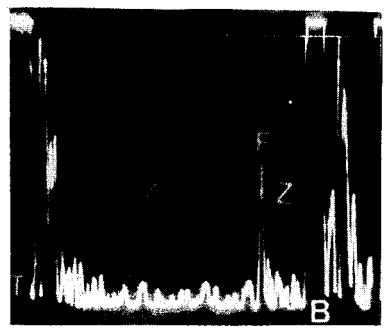

In the drawings, the reference numeral 1 represents an ultrasonic absorber; 2, a back surface of the reference block; 3, a plug; 4, a calibration hole; 5, a test surface; and 6, an angle. In ultrasonic examination, a search unit is contacted with the test surface 5 to detect an indication from the calibration hole 4, and the working sensitivity of ultrasonic examination is adjusted. In FIGS. 1 and 2, the ultrasonic absorbers are bonded, cast or brazed onto a back surface of a conventional block. In FIG. 3, the ultrasonic absorber is fitted in the back surface of a block and set by bonding, casting or brazing. In FIG. 4, the angle 6 is set at a desired value so that the block can be used both in a straight beam test and in an angle beam test. The ultrasonic absorber is fitted in the back surface of the block and set by bonding, casting or brazing.

The ultrasonic absorber can be secured to the back surface of the block by bonding, casting, brazing, etc. The method of securing must, however, be selected so as not to hamper transmission of ultrasonic waves from the reference block to the ultrasonic absorber.

When the reference block in accordance with this invention is used, no ghost indication is noted even at relatively high pulse repetition frequencies. Or if ghost indication is noted, it is only a trace. Accordingly, the reliability in working sensitivity is excellent. The reason for the substantial absence of ghost indication is not entirely clear, but it is theorized as follows: Every time ultrasonic waves reach the back surface of the block, they are partly transmitted to the ultrasonic absorber secured to the back surface of the block. The ultrasonic energy which has been transmitted is converted into a heat energy in the ultrasonic absorber. As a result, the amount of ultrasonic waves reflected at the back surface of the block decreases. The ultrasonic waves which reciprocate many times within the block quickly decay because they are partly absorbed by the ultrasonic absorber every time they are reflected at the back surface of the block. Thus, when the next ultrasonic pulse is sent, the ultrasonic waves attributed to the previously sent ultrasonic pulse and the residual ultrasonic waves in the block are so weak as to cause no trouble in practice. Consequently, the decrease of the reliability in working sensitivity which is due to the superimposition and hampering of ghost indication upon the indication of the calibration hole can be prevented.

According to this invention, the excellent reliability of working sensitivity with substantially no ghost indication can be achieved at a relatively high pulse repetition frequency, especially at a frequency in the range of 250 to 2,000 Hz. The reference block for ultrasonic examination and the ultrasonic flaw detecting method in accordance with this invention using this block has made it possible for the first time to perform accurate flaw detection at rapid scanning speeds.

The ultrasonic examination method of the invention can be applied to a very wide range of fields, and contributes particularly to the aircraft industry, automotive industry, machinery industry, iron and steel working industry, and non-ferrous metal working industry, etc.

The following Examples illustrate the present invention more specifically.

EXAMPLE 1

A block of quenched and tempered nickel-chromium-molybdenum steel according to SNCM 439 (AISI 4340 steel) was prepared in the shape shown in FIG. 1 (diameter 50 mm, length 180 mm, calibration hole diameter 1 mm, calibration hole depth 30 mm). A phenolic resin plate having a thickness of 5 mm, 10 mm or 15 mm, an attenuation coefficient of 0.7 dB/mm at 2.25 MHz and an acoustic impedance of $3.6 \times 10^6$ kg/m$^2$s was bonded to the back surface of the block by means of an epoxy-type adhesive to prepare test blocks. Each of the test blocks were examined by using ultrasonic waves having a frequency of 2.25 MHz. It was found that even at a pulse repetition frequency of 500 Hz, the ghost indication was so small as not to hamper the adjustment of working sensitivity. A sufficient thickness of the phenolic resin plate was found to be 5 mm.

EXAMPLE 2

A block having the same shape and dimension as STB-G, V15-1 stipulated in JIS Z-2345 (having the shape shown in FIG. 2) was prepared from quenched and tempered steel of SNCM 439. The same phenolic resin plate as in Example 1 having a thickness of 5 mm was bonded to the back surface of the block by means of an epoxy-type adhesive to form a test block. The test block was examined by using ultrasonic waves having a frequency of 2.25 MHz. The results are shown in FIG. 5. In FIG. 5, a-1 and a-2 show oscilloscope screen pictures obtained when the phenolic resin plate was not bonded to the test block; b-1 and b-2 show oscilloscope screen pictures obtained when the phenolic resin plate was bonded to the test block. In a-1 and b-1, the pulse repetition frequency is 125 Hz, and in a-2 and b-2, the pulse repetition frequency is 500 Hz. In FIG. 5, T represents an initial pulse; F, an indication of the calibration hole; B, back reflection; and Z, ghost indication.

It is seen from FIG. 5 that when the pulse repetition frequency is low, there is no great difference in oscilloscope screen pictures irrespective of the presence of the ultrasonic absorber, but when the pulse repetition frequency is as high as 500 Hz, the effect of the ultrasonic absorber increases, and the ghost indication is markedly reduced.

EXAMPLE 3

Test blocks having the same shape and dimension as STB-G, V15-1 stipulated in JIS Z-2345 (having the shape shown in FIG. 2) were prepared from quenched and tempered steel of SNCM 439. Each block was allowed to stand upright with its back surface turned upward. An adhesive tape was wound about that side surface which was near the back surface to form a frame. A mixture of 33% by weight of an epoxy resin and 67% by weight of iron powder was cast to a thickness of about 5 mm onto the back surface of one block. Furthermore, a mixture of 16% by weight of an epoxy resin, 79% by weight of iron powder and 5% by weight of hard rubber powder was cast onto the back surface of another block. The epoxy resin-iron powder ultrasonic absorber had an attenuation coefficient of 3 dB/mm and an acoustic impedance of about $7 \times 10^6$ kg/m$^2$s, and the epoxy resin-iron powder-rubber powder ultrasonic absorber had an attenuation coefficient of more than 5 dB/mm and an acoustic impedance of about $6 \times 10^6$ kg/m$^2$s.

The above test blocks were examined by using ultrasonic waves having a frequency of 2.25 MHz. The results are shown in FIG. 6.

In FIG. 6, c-1 and c-2 show oscilloscope screen pictures obtained when the mixture of epoxy resin and iron powder was used as the ultrasonic absorber; and d-1 and d-2 show oscilloscope screen pictures obtained when the mixture of epoxy resin, iron powder and hard rubber powder was used as the ultrasonic absorber. In c-1 and d-1, the pulse repetition frequency was 500 Hz, and in c-2 and d-2, the pulse repetition frequency was 1,000 Hz. In FIG. 6, T represents an initial pulse; F, an indication of the calibration hole; B, back reflection; and Z, ghost indication.

It is seen from FIG. 6 that when the pulse repetition frequency is 500 Hz, the ghost indication is only a trace, but more ghost indication is noted at a pulse repetition frequency of 1,000 Hz. The effect of the ultrasonic absorbers used in this Example was greater because they had larger attenuation coefficients and acoustic impedances. As a result, the ghost indication was markedly reduced, and the adjustment of working sensitivity was easy. The decrease of the reliability of working sensitivity due to the superimposition and hampering of the ghost indication on the indication of the calibration hole could be prevented.

EXAMPLE 4

A block having the same shape and dimension as STB-G, V15-1 stipulated in JIS Z-2345 (having the same shape as in FIG. 2) was prepared from quenched and tempered steel of SNCM 439. The block was allowed to stand upright with the back surface turned upward. A glass plate was bonded to that side surface of the test block which was near the back surface to form a frame. A solder consisting of 40% of lead and 60% of tin and having an attenuation coefficient of about 0.2 dB/mm and an acoustic impedance of $24 \times 10^6$ kg/m²s was applied to the back surface of a height of about 4 mm. The test block was examined by using ultrasonic waves having a frequency of 2.25 MHz. The results are shown in FIG. 7. In FIG. 7, e, f and g show oscilloscope screen pictures obtained when the pulse repetition frequency was 500 Hz, 1,000 Hz and 2,000 Hz, respectively. In FIG. 7, T represents an initial pulse; F, an indication of the calibration hole; B, back reflection; and Z, ghost indication.

It is seen from FIG. 7 that at a pulse repetition frequency of 500 Hz, no ghost indication was noted, and slight ghost indication was noted at 1,000 Hz. Ghost indication appeared clearly when the pulse repetition frequency was 2,000 Hz, but it was not to such an extent as to hamper detection of the indication of the calibration hole. The ultrasonic absorber in this Example showed the greatest effect among the Examples given in this application, and it was found that ultrasonic absorber alloys applied by casting or brazing are especially effective for reducing ghost indication.

What we claim is:

1. A reference block for ultrasonic examination, said blocking having an ultrasonic absorber secured to its back surface and producing substantially no ghost indication at a pulse repetition frequency of 250 to 2,000 Hz.

2. The block of claim 1 wherein the ultrasonic absorber has an attenuation coefficient at a test frequency of 2.25 MHz of at least 0.1 dB/mm and an acoustic impedance of at least $1.5 \times 10^6$ kg/m²s.

3. The block of claim 1 or 2 wherein the ultrasonic absorber is composed of a mixture of an epoxy resin and iron powder.

4. The block of claim 1 or 2 wherein the ultrasonic absorber is composed of a mixture of an epoxy resin and tungsten powder.

5. The block of claim 1 or 2 wherein the ultrasonic absorber is composed of a lead alloy containing at least 30% by weight of lead.

6. The block of claim 1 or 2 wherein the ultrasonic absorber is composed of a mixture of a lead alloy containing at least 30% by weight of lead, and tungsten particles.

7. A method for ultrasonic examination, which comprises using a reference block having an ultrasonic absorber secured to its back surface, and wherein the ultrasonic examination is conducted at a pulse repetition frequency of 250 to 2,000 Hz.

8. The method of claim 7 wherein the ultrasonic absorber has an attenuation coefficient at a test frequency of 2.25 MHz of at least 0.1 dB/mm and an acoustic impedance of at least $1.5 \times 10^6$ kg/m²s.

9. The method of claim 7 or 8 wherein the ultrasonic absorber is composed of a mixture of an epoxy resin and iron powder.

10. The method of claim 7 or 8 wherein the ultrasonic absorber is composed of a mixture of an epoxy resin and tungsten powder.

11. The method of claim 7 or 8 wherein the ultrasonic absorber is composed of a lead alloy containing at least 30% by weight of lead.

12. The method of claim 7 or 8 wherein the ultrasonic absorber is composed of a mixture of a lead alloy containing at least 30% by weight of lead and tungsten particles.

* * * * *